(12) United States Patent
Myers et al.

(10) Patent No.: US 6,816,791 B2
(45) Date of Patent: Nov. 9, 2004

(54) ASSAY METHODS FOR HYDRATABLE CEMENTITIOUS COMPOSITIONS

(75) Inventors: David F. Myers, Acton, MA (US); Felek Jachimowicz, Brookline, MA (US); Joanna D. Blanchard, Merrimac, MA (US); Neal S. Berke, N. Chelmsford, MA (US); Josephine H. Cheung, Waltham, MA (US); Paul J. Sandberg, Beverly, MA (US); Frank G. Serafin, Peabody, MA (US); Peter V. Coveney, Woodford Green (GB)

(73) Assignee: W. R. Grace & Co.-Conn., Columbia, MD (US)

( * ) Notice: Subject to any disclaimer, the term of this patent is extended or adjusted under 35 U.S.C. 154(b) by 70 days.

(21) Appl. No.: 10/182,114
(22) PCT Filed: Jan. 30, 2001
(86) PCT No.: PCT/US01/03002
§ 371 (c)(1), (2), (4) Date: Oct. 15, 2002
(87) PCT Pub. No.: WO01/55047
PCT Pub. Date: Aug. 2, 2001

(65) Prior Publication Data
US 2004/0064265 A1 Apr. 1, 2004

Related U.S. Application Data
(60) Provisional application No. 60/179,362, filed on Jan. 31, 2000.

(51) Int. Cl.[7] ............................ G06F 19/00; G01N 30/00
(52) U.S. Cl. ............................ 702/25; 702/32; 73/61.72
(58) Field of Search .............................. 702/25, 32, 22; 73/61.71, 61.72; 106/720, 756; 436/174, 180, 72

(56) References Cited

U.S. PATENT DOCUMENTS

| 4,259,868 A | 4/1981 | Rao et al. ..................... 73/597 |
| 4,436,555 A | 3/1984 | Sugama et al. ............... 106/85 |
| 4,478,806 A | 10/1984 | Ball et al. .................... 423/328 |
| 4,797,160 A | 1/1989 | Salyer .......................... 106/96 |
| 4,968,734 A | 11/1990 | Gaidis et al. .................. 524/5 |
| 5,122,191 A | 6/1992 | Morozumi et al. ......... 106/811 |
| 5,246,496 A | 9/1993 | Sugama et al. ............. 106/690 |
| 5,285,679 A | 2/1994 | Jackson et al. ............... 73/61 |
| 5,362,321 A | 11/1994 | Larsen ....................... 106/713 |
| 5,508,200 A | 4/1996 | Tiffany et al. ............... 436/44 |
| 5,992,223 A | 11/1999 | Sabins et al. ............... 73/64.42 |

FOREIGN PATENT DOCUMENTS

| GB | 2 261 955 A | 2/1993 | .................... 33/38 |
| WO | WO 01/55047 A2 | 2/2001 | |
| WO | WO01/55047 A3 | 2/2001 | .................... 33/38 |

OTHER PUBLICATIONS

International Search Report, May 8, 2001, International Application No. PCT/US01/03002, International Filing Date Jan. 30, 2001.

*Primary Examiner*—Michael Cygan
(74) *Attorney, Agent, or Firm*—Craig K. Leon; William L. Baker

(57) ABSTRACT

A novel methodology for rapid, cost-efficient discovery, identification, or improvement of additives and/or admixtures for hydratable cementitious compositions. Multiple formulations comprising hydratable cementitious compositions are deposited into a plurality of receptacles. A first assay output is obtained, such as through x-ray diffraction, which is then correlated to provide a second assay output value corresponding to physical or chemical properties of the cementitious compositions.

18 Claims, 3 Drawing Sheets

ASSAY METHODS FOR HYDRATABLE CEMENTITIOUS COMPOSITIONS

This application claims the benefit of Provisional Application No. 60/179,362, filed Jan. 31, 2000.

FIELD OF THE INVENTION

The present invention relates to a method for testing hydratable particle compositions, and more particularly to an automated assay method for testing hydratable cementitious compositions containing additives and/or admixtures and predicting physical or chemical properties of these compositions.

BACKGROUND OF THE INVENTION

The terms "additive" and "admixture" are generally understood in the cement and concrete arts. The term "additive" generally refers to an agent that is operative to increase grinding efficiency of cement clinker, to reduce the pack setting of processed cement, or otherwise to modify one or more properties or to increase efficiency of the cement grinding operation. The term "additive" thus usually refers to any addition, such as a processing addition, which aids in the manufacture and handling of the cement product, or a functional addition that modifies the use properties of the cement. On the other hand, the term "admixture" refers to a material other than water, aggregate (e.g., crushed stones or gravel, sand), and cement which might be added to concrete before or during its mixing. Admixtures can function by several mechanisms, such as (1) dispersions of the cement or particle in the aqueous phase of concrete (e.g., slurry); (2) alteration of the normal rate of hydration of the cement, in particular the tricalcium silicate phase; (3) reaction with the by-products of the hydrating cement, such as alkalies and calcium hydroxide; and (4) no reaction with either the cement or its by-products.

The terms "additive" and "admixture" sometimes overlap. It may be the case, within the present application, that the terms can be used synonymously in reference to agents for modifying cement, concrete, or other cementitious compositions, whether in dry particle, wet slurry (or paste), or hardened form (e.g., formed into a structure such as a foundation wall, block, brick, paver, etc).

To this point in the industry, the testing of additives and admixtures has involved production of relatively large mortar or concrete samples. A mortar or concrete sample would usually be made by mixing Portland cement with water and fine aggregate (in the case of mortar) or fine and coarse aggregate (in the case of concrete), after which an additive and/or admixture can be added. If the fluidity or slump properties were being measured, the cementitious composition would be poured into a standard slump cone (approximately one foot high). If the corrosion resistance were being tested, the sample would be cast into approximately 2–4"×4–8" cyclinders or 6"×5"×12" brick rectangles (or "mini-beams"). If the compressive strength of mortar was being tested, two-inch cubes were made, and cylinders were made if the compressive strength of concrete were being tested. Thus, as a general proposition, the current techniques and methodologies in the industry for testing, analyzing, or evaluating one or more physical or chemical properties of cementitious materials, optionally containing additives or admixtures, typically involved large volumes of materials and laborious, time-consuming testing on a sample-by-sample basis.

In U.S. Pat. No. 6,009,419, Coveney and Fletcher describe a method for predicting the thickening (setting) time of a cement slurry from the Fourier transform infrared spectra (FTIR) of a cement powder or cement slurry. The thickening time of a cement slurry is of principal importance in the field of oilwell cementing and is dependent upon a number of properties including the mineral composition of the cement. However, the authors only practice a method for predicting the thickening time from the FTIR spectra of the cement powder. The FTIR spectrum of the unhydrated cement powder contains information on the cement composition and is also somewhat affected by other non-chemical properties, such as particle size distribution, crystallographic defects in cement grains, and compositional variations between cement grains, all of which may influence thickening times.

In the present invention, however, a method for predicting compressive strength of mortar is described which involves the analysis of Raman spectra of cement paste (hydrated cement powder or cement slurry) samples. This invention is fundamentally different from that in U.S. Pat. No. 6,009,419 in that (1) spectrum are being recorded of cement paste instead of cement powder, (2) thickening time and compressive strength are different physical properties (and it is believed by the present invenors that the ability to predict the former does not guarantee the ability to predict the latter), and (3) Raman spectroscopy as an analytical technique is fundamentally different from infrared spectroscopy.

Moreover, a particularly differentiating feature of the present invention from that described in the '419 patent is that the present inventors found that the effect of additives on compressive strength could not be predicted from infrared spectra (specifically photoacoustic spectroscopy) of the cement paste (slurry). The present inventors discovered that Raman spectrum recorded on cement paste samples, unlike the infrared spectrum, did permit detection of differences in cement chemistry induced by additives which resulted in changes in compressive strength.

SUMMARY OF THE INVENTION

One objective of the present invention is to provide a novel and inventive methodology for rapid and cost-efficient discovery or improvement of additives and admixtures for hydratable cementitious compositions. Multiple formulations comprising hydratable cementitious compositions are deposited into a plurality of receptacles which are assayed by certain spectroscopic techniques. This first assay output value is used to predict, through a correlating model, a second assay output value corresponding to one or more physical or chemical properties of said cementitious compositions. The methodology is applicable to the analysis and optimization of the chemical and physical properties of mixtures of cement and water optionally containing fine aggregate and cement additives or concrete admixtures, but can also be applied to a multitude of formulated materials.

In particular, methodologies of the invention are useful for the analysis and optimization of physical or chemical properties of mixtures of cement and water optionally containing fine aggregate and cement additives or concrete admixtures. For example, automated techniques of the present invention are useful for producing milliliter-scale cement slurry (or paste) or mortar samples with or without additive(s) and/or admixtures(s). The automated techniques can produce an enormous volume (hundreds and even thousands) of slurry (or paste) or mortar samples per week. The cement paste or mortar samples may differ in accordance with variations as to cement type, water-to-cement ratio, fine aggregate type, additives or admixtures type (and/or amounts), and filler material type and/or amount. Exemplary samples of the invention may be provided as a plurality of receptacles (such as small cuvettes in a rack or tray) or be contained on a substrate (such as a cement slab, plastic tray, plexiglass or glass sheet having pockets or indentations for containing samples and can be of any size and shape (preferably cylindrical or cubical). Exemplary cement paste or mortar samples (with or without additives/admixtures) are analyzed (concurrently or in parallel) to ascertain one or more properties of the cement slurry, cement paste, or mortar. These properties may include, but are not limited to, chemical composition, crystallographic structure, particle size distribution, micro-rheology (such as plastic viscosity, yield stress, etc.), ultrasonic response, electrical response, and compressive strength, among others.

Exemplary spectroscopic techniques suitable for use in process of the invention comprise Raman spectroscopy, which is most preferred, and also other preferred techniques, including x-ray diffraction, x-ray fluorescence, calorimetry, thermal gravimetric analysis, differential thermal analysis, loss on ignition, nuclear magnetic resonance, scanning electron microscopy, impedance spectroscopy, and ultrasound, or combinations of the foregoing. Such spectroscopic analytical techniques may be conducted at discrete times or over time intervals. The samples may be analyzed at any age (with age defined as the time after the addition of water), but the preferred age is between 0 and 28 days, more preferably between 0 and 2 days, and more preferably between 0 and 1 day. The results of the analyses are then used to predict, through a correlating model, a second assay output value corresponding to one or more physical or chemical properties of the samples. The knowledge gained from this analysis is then used to formulate an optimal cement additive or concrete admixture system for a given application and desired set of physical or chemical properties.

An exemplary assay method of the invention for testing cementitious compositions thus comprises: combining a plurality (e.g., preferably more than 2 and preferably at least 12) of additives and/or admixtures with water in individual receptacles; adding hydratable particles (e.g., cement, fly ash, slag, or combination thereof) and optionally fine aggregate to these receptacles to make a slurry or mortar; mixing the contents simultaneously with individual, variable speed overhead mixers for a desired time period (e.g., 30 seconds); dividing each of the mixed slurries or mortars into several new, individual receptacles; curing (or aging) the slurry or mortar samples in a controlled environment (e.g., controlled temperature, humidity, atmosphere, etc.); assaying the aged (e.g., ranging from 0 to 28 days) slurry or mortar samples by one or more technique; and optionally predicting, through a correlating model, a second assay output value corresponding to one or more physical or chemical properties of the samples. The effect of the amounts of additives or admixtures may be tested for their effects in terms of varied predetermined amounts.

Further features and benefits of the invention are described in further detail hereinafter.

DETAILED DESCRIPTION OF EXEMPLARY EMBODIMENTS

Figure 1:
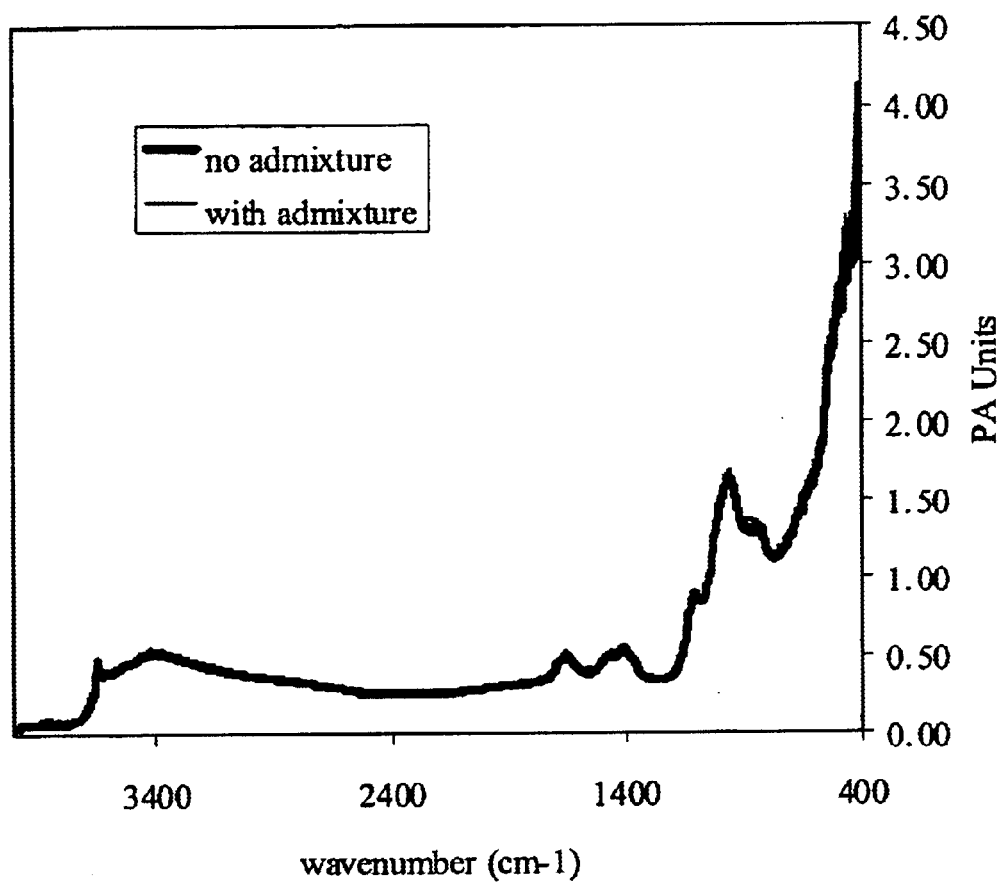
FIG. 1 (PRIOR ART) is a graphic representation illustrating infrared (IR) spectroscopy which is unable to distinguish the effect, in two cement paste samples, of the presence or effect of an admixture.

The term "cementitious" as may be used herein refers to a composition containing a hydratable binder, such as Portland cement, gypsum cement, and/or particles such as limestone, hydrated lime, fly ash, blast furnace slag, pozzolans, and silica fume or other materials commonly included in such cements. A cementitious composition, provided in the form of a slurry (or paste), will therefore comprise such a hydratable binder (e.g., Portland cement) in combination with water; and a cementitious composition that is provided in the form of a mortar will therefore comprise such a hydratable binder (e.g., Portland cement) in combination with water and fine aggregate. Exemplary methods of the present invention involve placing or dispensing given volumes of admixture and water into a plurality of receptacles (e.g., preferably more than 2 and at least 12), which may be cuvettes, indentations in a plastic or glass tray, in test tubes, etc.; and adding hydratable binder, and optionally a fine aggregate (e.g., sand), to make a cementitious slurry. Average sample size of the compositions is preferably $10^{-3}$ to 100 cubic centimeters (cc), and more preferably 0.1–10.0 cc.

A preferred method of the present invention for dispensing one or more admixtures or additives and water into a plurality of receptacles (e.g., cuvettes) is through the use or automated positive displacement devices (e.g., syringes) or syringe pumps. A preferred method for adding solids (e.g., hydratable binder, fine aggregate) into the receptacles is by first weighing out the desired amounts of these components using a balance, and then transferring the solid material to the receptacles. The contents of the receptacles are mixed simultaneously for a controlled length of time using, for example, individual, variable speed, overhead stirrers with impeller blades manufactured from a nonstick material. Optionally, the additives and/or admixtures to be tested can be added to the plurality of receptacles after mixing the water and solid materials. These "master batches" of slurry or mortar are each divided into several new, individual receptacles. Average sample size of the compositions is preferably $10^{-3}$ to 100 cubic centimeters (cc), and more preferably 0.1–5.0 cc. Preferred assay receptacles are polymeric trays that are injection molded to yield indentations for receiving the samples. The trays may comprise high density polyethylene (HDPE), polypropylene, polyethylene terephthalate, or other injection-moldable polymer materials. They may also comprise metal (preferably having a nonstick coating, such as TEFLON® brand, e.g., polyfluoroethylene), paper (e.g., cellulosic), or other materials that could be used as a supportive substrate for cementitious materials; although plastics such as HDPE are most preferred because they can be molded or injeciton-molded with indentations or cavities in a convenient manner. These indentations or cavities can be of any shape or size (volume), but preferably are cylindrical or cubical (or rectangular). The mortar or slurry samples are aged under controlled conditions (e.g., temperature, atmosphere, and humidity) for a desired length of time (e.g., 0 to 28 days). After reaching the desired age, the samples are assayed by one or more techniques. The samples can be screened by the assays of the invention either simultaneously; or, alternatively, they can be screened in parallel.

For example, after the "master batches" are divided into individual receptacles, the individual trays are bar-coded for identification and stored under controlled conditions for a desired time. The environment may be controlled, for example, in terms of temperature, humidity, or atmospheric pressure. The samples are cured in this controlled environment for a desired length of time (e.g., 0 to 28 days).

Exemplary assays useful for the present invention include, but are not limited to, the use of Raman Spectroscopy. X-Ray Diffraction (XRD); and Calorimetry.

Raman spectroscopy is a well-established analytical technique for identification and quantification of the chemical components of a sample. The Raman effect results from the interaction of light with a molecular bond. A sample is energized with a high-power, narrow-wavelength energy source (usually a laser). The molecule is temporarily energized to an unstable state. When the molecule drops back into its ground state, the molecule emits photons with either more, less, or the same energy (frequency) as the incident light. The amount of this change in frequency, or wavelength shift, and the intensity of the signal depends on the size, shape, and bond strength of the molecule. Hence, each Raman spectrum is a distinct "fingerprint" of the molecule. Unlike IR spectroscopy, the vibrational modes that are Raman active are those accompanied by a change in polarizability rather than dipole moment.

X-ray diffraction is a commonly used technique for the identification and quantification of solid-state, crystalline materials. A sample is illuminated with x-rays of a fixed wave-length. Both the intensity of the reflected radiation and the reflection angle is recorded. As no two chemical substances form crystals with identical spacing of the planes in all analogous directions, the x-ray diffraction pattern is unique for each crystalline substance. The intensity of the diffraction peaks is a function of the quantity of the diffracting phase in the sample.

Calorimetric analytical techniques involve the measurement of heat that is evolved or absorbed during a chemical reaction. Calorimetry can either be performed isothermally or adiabatically. In the former case, the energy required to maintain a sample at a constant temperature is measured. In the latter, the sample is placed in an adiabatic chamber, and the temperature of the sample is measured. The profiles obtained can serve as a "fingerprint" to characterize the reactions taking place in a given sample. Calorimetry generally cannot be used, however, for identifying the specific reactants or reaction products.

Accordingly, exemplary methods of the invention comprise using one or more of the above-mentioned conventional assay techniques and methods on a plurality of hydratable cementitious compositions comprising at least one cement additive or admixture, obtaining a first output value, and correlating this output value with at least one chemical or physical property of the cementitious slurry (either in the wet or hardened state).

For example, exemplary physical and chemical properties include, but are not limited to, the degree of particle (e.g., cementitious binder) dispersion; rheology; bubble size or void distribution; surface tension; amount of hydration; degree of hydration; amount of C—S—H present or formed; phase composition; set time; porosity or percolation characteristic; compressive strength (including 7 and 28 day compressive strength); shrinkage; corrosion resistance and others.

As summarized previously, an exemplary assay method comprises providing a plurality of receptacles; dispensing admixture or additive and water into these receptacles; adding the hydratable particles (e.g., Portland cement), and, optionally, fine aggregate; mixing the cement paste or mortar composition using a mechanical device; dividing the plurality of "master batches" into several, new, individual receptacles; optionally aging the paste or mortar samples in a controlled environment; assaying the hydratable slurry or mortar compositions containing at least one additive or admixture to obtain first assay output values (e.g., which may be in form of electrical output such as voltage from a sensor, for example of Raman device, x-ray diffraction device, calorimeter, etc., or can be in the form of data, such as numeral values); inputting said first assay output values into a central processing unit (computer); processing said inputted first assay output values using a correlating function operative to provide a second assay output value; and providing an indication of said second assay output value. The additive(s) or admixture(s) to be tested can be optionally added to the plurality of receptacles after mixing the water and solid materials.

For example, if Raman spectroscopy is used for the assay, then the first assay output values are most likely to be in the form of numerical data (e.g., absorbance spectra showing absorbance as a function of wave number or wave length).

Thus, in one preferred embodiment, a plexiglass (or plastic) sheet (tray) having small dimples or pockets on one major face of the sheet, is used as a plurality of receptacles for containing a plurality of hydratable cementitious compositions having different combinations of additives or admixtures (and/or varied amounts thereof). For example, a cementitious slurry, optionally containing cement additive and/or concrete admixture, is deposited in uniform volumes into the dimples using an automated dispensing device. Subsequently, the samples can be screened, such as on a parallel basis (all at the same time) using a plurality of sensors (e.g., for Raman analysis) or a sequentially (sample by sample) by moving a sensor row by row across the sheet tray. The signal output from the sensor is then fed (e.g., by known electrical or electronic means) to a central processing unit (such as in a laptop computer) which then processes these first array signal output values by subjecting them to a correlation program inputted by the operator (such as into computer memory or located on storage media such as floppy disk, hard disk, or other storage device. The correlation program then transforms the first assay value into a second assay value that corresponds with a chemical or physical characteristic of the cement sample (such as 28-day compressive strength), so that the operator can determine the effect of the individual additives or admixtures being tested on the physical property. The derived second assay value can be indicated on a computer monitor screen, on a hard copy print-out, or otherwise manifested on some sort of tangible or readable form that can be comprehended by the user.

Correlation programs or methods suitable for fulfilling the purposes of the present invention are known for converting first array signal output values (derived from Raman sensors, for example) into the second array signal output values that correspond with one or more chemical or physical properties of the cement compositions (for e.g., 28-day compressive strength). The ability to select, create, modify, or apply such correlation programs are believed to be within the knowledge of those skilled in the art, or could otherwise be implemented without undue experimentation. For example, one such correlation method or tool may be found by reference to artificial neural network models. Neural network models are computer programs that attempt to reproduce certain logic operations of human thought processes by using a collection of neuron-like entities (or nodes) to process data. Each node uses transfer functions (mathematical expressions) to combine numerous (e.g., 2 or more) numerical inputs into a single output. In the present invention, the input to the neural network model are the principal components of the spectral data (e.g., Raman, XRD, or calorimetry spectroscopic derivations) and the output is a physical or chemical property of mortar or cement paste (e.g., a property such as compressive strength).

Other exemplary correlation programs or methods that are believed by the present inventors to be suitable for fulfilling the purposes of the present invention may be derived from multivariate analytical methodologies that are used for predicting physical or chemical properties of cement pastes or mortars from spectral data. Multivariate data analysis is a collective term for methods that extract information from data tables. Two principal tools of multivariate data analysis are Principal Component Analysis (PCA) and Partial Least Squares regression (PLS). PCA transforms data in a matrix into a new coordinate system. PLS correlates the principal components of the input matrix (e.g., spectra data) to those of the output data (e.g., compressive strength).

A multivariate calibration model can be derived, for example, from a publication entitled "Rapid Cement Quality Control Method for Improved Oilfield Cement," T. L. Hughes, C. M. Methven, et al. (Copyright 1994, Offshore Technology Conference), particularly from pages 643–654, which are incorporated by reference herein. It was explained that a critical factor for determining the performance of complex slurry formulations used in oilfield cementing was the variability in the properties of the cement, and that rapid and accurate cement quality control methods based on Fourier transform infrared spectroscopy ("FTIR") could be successfully deployed for determining the components of cements which were key to their performance. The FTIR spectrum of the dry cement powder was a unique "snapshot" signature of cement composition and particle size. The extent of cement "aging" was encoded in the measurement. Multivariate calibration models based on a large database of cements allowed the spectrum to be transformed to a quantitative analysis of the clinker phases, the sulphate, hydroxide and carbonate minerals and minor oxides. The method was thus useful for quantitative analysis of cement blends. The use of the method allowed for rapid screening of cements and rejection of those which did not meet specifications, and more efficient testing of slurry formulations prior to field use, as well as rapid evaluation of local cement supplies in newly developed oilfields.

While FTIR has been used to analyze elemental composition of cements to determine constituent minerals to predict setting times, the present invention seeks a method for the rapid assay of a cement paste or mortar to predict compressive strength. Thus, in exemplary methods of the invention, Raman spectroscopy is used to analyze cement paste samples and/or samples containing one or more additives or admixtures. Unlike IR spectroscopy, the vibrational modes of samples tested using Raman spectroscopy are those accompanied by a change in polarizability rather than dipole moment.

The following examples are useful for illustrating the foregoing discussion.

EXAMPLE 1 (PRIOR ART)

Cement paste samples were made by mixing water and Portland cement in water/cement ratio (by weight) of 0.4. Cement paste samples are thus tested two at a time, the first sample containing no admixture, and the second containing triisopropanolamine (TIPA) in the amount of 0.015% by dry weight based on weight of cement.

Infrared spectroscopy was used on both cement paste samples, and it was discovered that the effect of admixture (e.g., TIPA) on compressive strength of the cement sample could not be predicted through comparison of the infrared spectra (specifically photoacoustic spectroscopy) of the cement pastes. As shown in FIG. 1, the photoacoustic spectra for the two cement paste samples, taken at two days after mixing, were nearly identical. Photoacoustic spectroscopy was unable to detect a difference between the cement paste with and without the admixture; inability is due to the overlapping spectra of the two samples shown in FIG. 1.

EXAMPLE 2

Two cement samples, one with admixture and one without admixture, made as described above in Example 2, were this time subjected to Raman spectroscopy. Preferably, the Raman spectroscopic technique should be used within 28 days of mixing the cement paste samples, and more preferably it should be used within 2 days and most preferably within 24 hours after mixing.

Where two or more samples are to be tested using Raman spectroscopy, it is preferred to run the tests in parallel (e.g., using multiple sensors for simultaneous readings) but the spectroscopic data can also be recorded in series. Furthermore, it is envisioned that Raman spectra can be recorded over any wavelength range, but most preferably between 400 and 2000 $cm^{-1}$.

Figure 2:
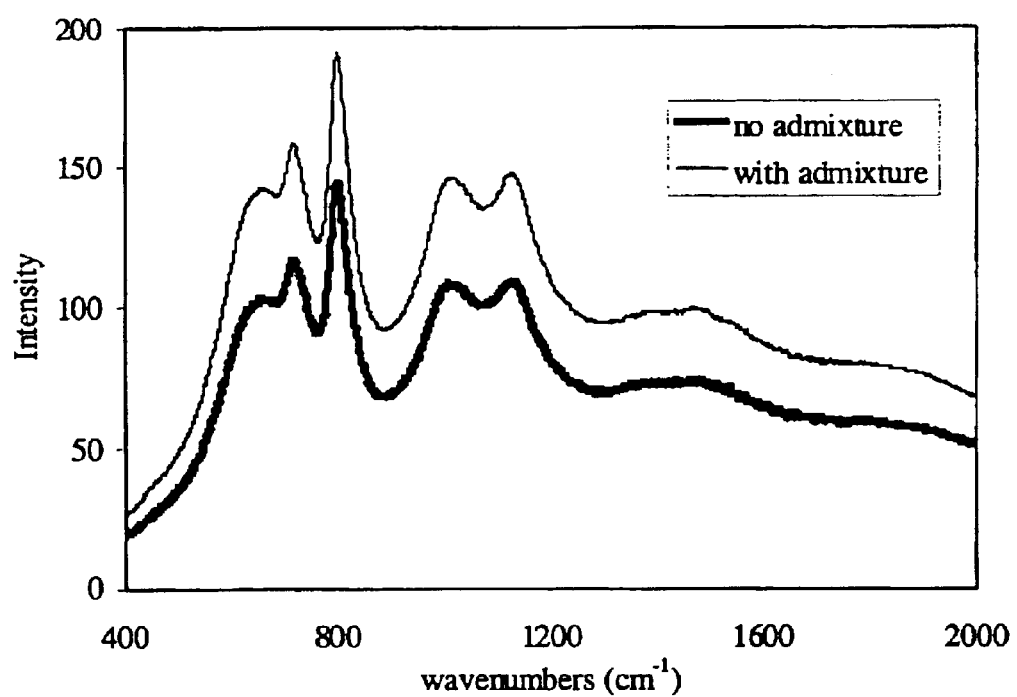
FIG. 2 is a graphic representation illustrating different Raman spectra of two cement paste samples, clearly illustrating the difference in effect of an admixture in one of the samples, in accordance with an exemplary method of the present invention.

As shown in FIG. 2, the differences of Raman spectra taken from two-day old cement pastes, one sample containing admixture (e.g., TIPA) and one without admixture, are visually apparent. The two cement pastes (one with admixture at same concentration; and one without admixture) were the same as those made for Example 1. According to FIG. 2, the presence of the admixture was evidenced by increased Raman signal intensity.

EXAMPLE 3

Two cement samples, one with admixture (TIPA) and the other without admixture, made as described in Example 1, were subjected to another preferred method of the present invention, this time calorimetric spectroscopy using an isothermal calorimeter.

Figure 3:
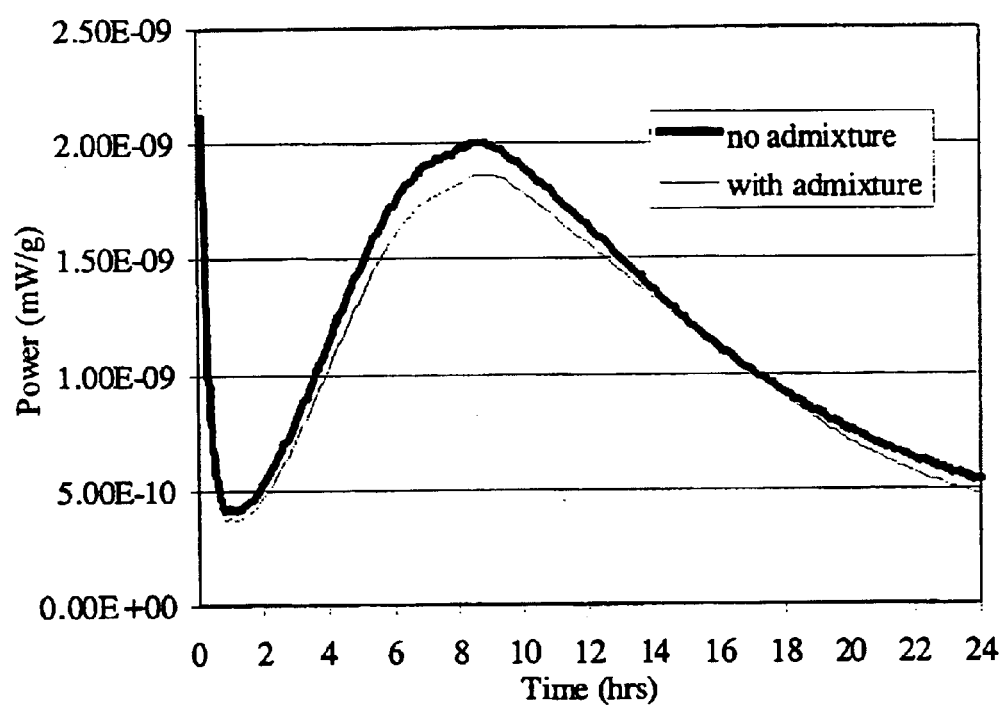
FIG. 3 is a graphic representation of calorimetric spectra of two cement samples aged between 0 and 24 hours, again showing difference in effect of an admixture, in accordance with another exemplary method of the present invention.

Calorimetric spectra are preferably recorded on the two cement samples within 48 hours, and more preferably within 24 hours, and most preferably within 1 hour, of mixing the cement samples. As shown in FIG. 3, differences between Raman spectra for the two cement pastes can be seen. The paste containing the admixture has a different profile than the paste without admixture, indicating either a difference in the chemical reactions (e.g., cement hydration) taking place, a difference in the respective rates of reaction, or both.

EXAMPLE 4

It is believed by the inventors that differences between cement pastes with admixture and cement pastes without admixture can be detected using x-ray diffraction (XRD) methods as follows. Two cement samples can be made as described in Example 1, and subjected to XRD preferably within 28 days of mixing, more preferably within 2 days, and most preferably within 1 day of mixing. The intensity of the reflected x-ray and the reflection angle by the cement paste sample is measured over the range of 0 to 180 degrees 2Θ, and more preferably over the range of 0 and 70 degrees 2Θ. It is believed by the present inventors that graphic illustration of the XRD data, plotted in terms of intensity against angle of reflection will demonstrate that the cement paste with admixture will show a decrease in signal intensity for the peaks corresponding to $C_3S$ and $C_2S$ formation in the cement paste samples.

In preferred embodiments of the invention, Raman spectroscopy is performed as part of the assay of a cementitious composition (first as control without the additive(s) or admixture(s) being tested) and then performed on samples containing the additives and/or admixtures to be tested. The samples may, for example, be moved sequentially across the sensor device so that the Raman spectra can be obtained, or the Raman spectra may be recorded in parallel using a plurality of sensors. The spectra, or first assay output values, are processed using a central processing unit and correlation program that screens for certain parts of the spectra (e.g., the computer can be programmed to measure certain parts or wavenumbers of the spectra), and these values can be transformed into second assay output values that serve as an indication, to the user, about one or more chemical or physical properties of the cement composition sample.

In preferred methods of the invention, additives or admixtures are dispensed into cuvettes that are retained in a tray or holder. Various cements (preferably from the customer site) and optionally other hydratable materials and fine aggregate are added into these cuvettes. The cuvettes are then mixed simultaneously with mechanical devices, such as with overhead stirrers. Optionally, the additives or admixtures can be added to the cuvettes after the addition and mixing of the solids and water. The individual "master batches" of the cement pastes or mortar compositions are then divided into one tray, or more preferably several trays, with receptacles for holding the samples. The trays are then bar coded for identification purposes and can, optionally, be placed in a controlled environment to be aged. When the samples achieve the desired age, the trays containing the samples are then moved, such as by automatic mechanism, under a sensor, such as Raman or XRD, which is connected to a central processing unit. The sensor provides first assay output values which are then converted by the central processor unit into a second assay output value using a correlating model that translates the first assay output value into an indication of one or more chemical or physical properties of the cement compositions being assayed.

The use of relatively small and numerous receptacles, such as cuvettes (0.5–10 cc in volume, for example) in high speed assay methods will bring enormous advantages and cost- and labor-savings. For testing of anti-corrosion properties of admixtures (for purposes of simulating the performance of anticorrosion admixtures in concrete reinforced by steel rebars), at least two (and preferably three) electrodes can be placed into the small cuvettes after the sample cementitious composition (and test admixtures) has been dispensed into and mixed in the cuvettes.

In further exemplary methods of the invention, a substrate which is made of hardened cement can be used for depositing various additives and/or admixtures to be tested. For example, a flat block having rows of indentations or depressions for holding drops or small samples of additives or admixtures can be used for automated assay scanning. This would be suitable, for example, in testing whether a number of components for a masonry block coating would be compatible. If one wanted to test 8 components, the components could be applied onto the cementitious substrate in a grid pattern, and the applied component samples could then be scanned, such as by light or UV analysis, for abnormal readings which could indicate that an undesired reaction was taking place between two or more of the components.

It is claimed:

1. An assay method for testing cementitious compositions, comprising:

providing a hydratable cementitious slurry composition comprising hydratable particles, water, and at least one additive or admixture, said particles comprising a hydratable binder selected from the group consisting of Portland cement, gypsum, fly ash, blast furnace slag, and silica fume; the term "additive" being defined as an agent that is operative to increase grinding efficiency of cement clinker, to reduce pack setting of processed cement, or to modify a property or increase efficiency of cement grinding operation; the term "admixture" being defined as a material other than water, crushed stones, crushed gravel, sand, or water that is added to concrete before or during its mixing;

providing a plurality of receptacles for containing sample volumes of said hydratable cementitious slurry composition and said at least one additive or admixture;

dispensing said hydratable cementitious slurry composition and said at least one additive or admixture into a plurality of receptacles;

assaying said hydratable slurry composition and said at least one additive or admixture dispensed into said receptacles to obtain first assay output values, said assaying being performed by x-ray diffraction, x-ray fluorescence, calorimetry, nuclear magnetic resonance, ultrasound, or combination thereof;

inputting said first assay output values into a central processing unit;

processing said inputted first assay output values using a correlating function operative to provide a second assay output value, said second assay output value corresponding with at least one property selected from the group consisting of dispersion, rheology, hydration, amount of CSH formation, phase compositions set time, porosity characteristic, percolation characteristic, compressive strength, shrinkage, and corrosion resistance; and providing an indication of said second assay output value.

2. The assay method of claim 1 wherein said hydratable cementitious slurry composition comprises Portland cement particles.

3. The assay method of claim 2 wherein said hydratable cementitious particles further comprise fly ash, blast furnace slag, or mixture thereof.

4. The assay method of claim 1 wherein said particles and water are introduced into said plurality of receptacles at a time different from said at least one additive or admixture.

5. The assay method of claim 1 wherein said plurality of receptacles is located on one substrate.

6. The assay method of claim 1 wherein said plurality of receptacles comprises cuvettes, said cuvettes being movably retained in a rack operative for moving the plurality of cuvettes from a first location to a second location.

7. The assay method of claim 1 wherein said first assay output values are inputted into a central processing unit and transformed into a spectra graph illustrated on a monitor screen.

8. The assay method of claim 1 wherein said first assay output values are inputted into a central processing unit, whereby second assay output values are obtained corresponding to compositional components of the assayed slurry composition samples.

9. The assay method of claim 5, wherein said substrate is cement.

10. The assay method of claim 1 wherein said hydratable cementitious slurry composition comprises at least one cement additive.

11. The assay method of claim 1 wherein said hydratable cementitious slurry composition comprises at least one admixture.

12. The assay method of claim 1 wherein said assaying of said hydratable slurry composition and said at least one additive or admixture to obtain first assay output values is performed by x-ray diffraction.

13. The assay method of claim 1 wherein said assaying of said hydratable slurry composition and said at least one additive or admixture to obtain first assay output values is performed by calorimetry.

14. The assay method of claim 13 wherein said calorimetry is performed isothermally.

15. The assay method of claim 13 wherein said calorimetry is performed adiabatically.

16. The assay method of claim 1 wherein said plurality of receptacles for containing sample volumes are no less than $10^{-3}$ cubic centimeters and no greater than 100 cubic centimeters.

17. The assay method of claim 1 wherein said plurality of receptacles for containing sample volumes are no less than 0.01 cubic centimeters and no greater than 10 cubic centimeters.

18. An assay method for testing cementitious compositions, comprising:

providing a hydratable cementitious slurry composition comprising hydratable Portland cement, water, and at least one additive or admixture; the term "additive" being defined as an agent that is operative to increase grinding efficiency of cement clinker, to reduce pack setting of processed cement, or to modify a property or increase efficiency of cement grinding operation; the term "admixture" being defined as a material other than water, crushed stones, crushed gravel, sand, or water that is added to concrete before or during its mixing;

providing a plurality of receptacles for containing sample volumes of said hydratable cementitious slurry composition and said at least one additive or admixture;

dispensing said hydratable cementitious slurry composition and said at least one additive or admixture into a plurality of receptacles;

assaying said hydratable slurry composition and said at least one additive or admixture dispensed into said receptacles to obtain first assay output values, said assaying being performed by x-ray diffraction, calorimetry, or combination thereof;

inputting said first assay output values into a central processing unit;

processing said inputted first assay output values using a correlating function operative to provide a second assay output value, said second assay output value corresponding with at least one property selected from the group consisting of dispersion, rheology, hydration, amount of CSH formation, phase composition, set time, porosity characteristic, percolation characteristic, compressive strength, shrinkage, and corrosion resistance; and providing an indication of said second assay output value.

* * * * *